(12) United States Patent
Chou et al.

(10) Patent No.: US 11,832,946 B2
(45) Date of Patent: Dec. 5, 2023

(54) SYSTEMS AND METHODS FOR PRODUCING STIMULI IN A VISUAL INTERFACE

(71) Applicant: Toyota Motor Engineering & Manufacturing North America, Inc., Plano, TX (US)

(72) Inventors: Chungchih Chou, Ann Arbor, MI (US); Muhamed Farooq, Ann Arbor, MI (US); Ercan Mehmet Dede, Ann Arbor, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 70 days.

(21) Appl. No.: 17/528,601

(22) Filed: Nov. 17, 2021

(65) Prior Publication Data

US 2023/0148927 A1    May 18, 2023

(51) Int. Cl.
*A61B 5/18* (2006.01)
*B60W 50/14* (2020.01)
*B60W 40/08* (2012.01)

(52) U.S. Cl.
CPC ............... *A61B 5/18* (2013.01); *B60W 40/08* (2013.01); *B60W 50/14* (2013.01); *B60W 2040/0872* (2013.01); *B60W 2050/146* (2013.01)

(58) Field of Classification Search
CPC ......... A61B 5/18; B60W 40/08; B60W 50/14; B60W 2040/0872; B60W 2050/146
See application file for complete search history.

(56) References Cited

U.S. PATENT DOCUMENTS

| 10,849,526 B1 * | 12/2020 | Demir ................... A61B 5/725 |
| 10,912,480 B2 | 2/2021 | Sridhar et al. |
| 11,091,168 B2 | 8/2021 | Chou et al. |

(Continued)

FOREIGN PATENT DOCUMENTS

| CN | 102512164 A | 6/2012 |
| CN | 105824418 A | 8/2016 |

(Continued)

OTHER PUBLICATIONS

Duart et al., "Evaluating the Effect of Stimuli Color and Frequency on SSVEP," Sensors 2021, vol. 21, issue 1, pp. 1-19.

(Continued)

*Primary Examiner* — Christopher E Leiby
(74) *Attorney, Agent, or Firm* — Christopher G. Darrow; Darrow Mustafa PC

(57) ABSTRACT

System, methods, and other embodiments described herein relate to controlling display attributes within a visual interface for enhancing stimuli and responses of a user. In one embodiment, a method includes selecting display attributes related to a first layer of an image and a second layer of the image, wherein the image is associated with an interface to control a component. The method also includes oscillating, at a frequency, between first values of the display attributes for displaying the first layer. The method also includes oscillating, at a harmonic of the frequency, between second values of the display attributes for displaying the second layer in parallel with the first layer until detecting a selection associated with the interface.

20 Claims, 4 Drawing Sheets

(56) References Cited

U.S. PATENT DOCUMENTS

| | | | |
|---|---|---|---|
| 2006/0098029 A1 | 5/2006 | Clas | |
| 2010/0045596 A1 | 2/2010 | De Leon | |
| 2016/0287157 A1* | 10/2016 | Simpson | A61B 5/168 |
| 2017/0210010 A1* | 7/2017 | Chen | B25J 13/00 |
| 2018/0039329 A1 | 2/2018 | Tumey | |
| 2018/0242834 A1 | 8/2018 | Hetling et al. | |
| 2021/0031778 A1 | 2/2021 | Farooq et al. | |
| 2021/0096705 A1 | 4/2021 | Rosenberg | |
| 2021/0240264 A1 | 8/2021 | Wilson et al. | |
| 2021/0276568 A1* | 9/2021 | Verbeke | B60R 21/01552 |
| 2022/0326771 A1* | 10/2022 | Pearce | A61B 5/7267 |

FOREIGN PATENT DOCUMENTS

| | | |
|---|---|---|
| EP | 3440494 A1 | 2/2019 |
| WO | 2017183436 A1 | 10/2017 |

OTHER PUBLICATIONS

Zhang et al., "The graph theoretical analysis of the SSVEP harmonic response networks," Cognitive Neurodynamics vol. 9, 2015, pp. 305-315.

Guney et al., "A Deep Neural Network for SSVEP-based Brain-Computer Interfaces," arXiv:2011.08562, Dec. 3, 2020, pp. 1-14.

Liu et al., "tACS Facilitates Flickering Driving by Boosting Steady-State Visual Evoked Potentials," arXiv:2003.12928, Mar. 29, 2020, pp. 1-17.

Brigell et al., "The effects of luminance and chromatic background flicker on the human visual evoked potential," Visual Neuroscience, vol. 13, issue 2, 1996, pp. 265-275.

Wei et al., "Stimulus Specificity of Brain-Computer Interfaces Based on Code Modulation Visual Evoked Potentials," PLoS ONE 11(5): e0156416, May 31, 2016, pp. 1-17.

Aminaka et al., "Chromatic and High-frequency cVEP-based BCI Paradigm," 2015 37th Annual International Conference of the IEEE Engineering in Medicine and Biology Society (EMBC), 2015, pp. 1906-1909.

Mu et al., "Frequency Superposition—A Multi-Frequency Stimulation Method in SSVEP-based BCIs," arXiv:2104.12187, Apr. 25, 2021, pp. 1-4.

Han et al., "Highly Interactive Brain-Computer Interface Based on Flicker-Free Steady-State Motion Visual Evoked Potential," Scientific Reports vol. 8, Article No. 5835, 2018, pp. 1-13.

Porciatti et al., "Retinal and cortical evoked responses to chromatic contrast stimuli: Specific losses in both eyes of patients with multiple sclerosis and unilateral optic neuritis," Brain, vol. 119, issue 3, Jun. 1996, pp. 723-740.

\* cited by examiner

SYSTEMS AND METHODS FOR PRODUCING STIMULI IN A VISUAL INTERFACE

TECHNICAL FIELD

The subject matter described herein relates, in general, to controlling a visual interface, and, more particularly, to controlling display attributes on the visual interface for producing stimuli and responses of a user.

BACKGROUND

Systems display visual interfaces for users to manage and control devices. For example, a user can touch or speak as inputs according to a displayed image on a device. In response, the device processes the input and responds with a visual change to the image or outputs audio. In various implementations, systems can use brainwaves from a user to receive an input or request a response. Using brainwaves may allow a user freedom to use hands for other tasks and reduce the distraction associated with controlling the device.

In one approach, a system uses visuals to stimulate a brainwave response from a user for control or alerts. For example, the system is a user interface displaying icons on a vehicle windshield that controls entertainment, safety, and temperature systems using brainwaves from an operator. The system varies an attribute of a displayed icon at a frequency associated with a task (e.g., navigation alert, radio control, etc.) for visual stimulation. However, these systems encounter difficulties enhancing or highlighting a task on a visual interface while maintaining operator awareness and engagement. As such, operator fatigue can increase particularly through prolonged exposure to visual stimulation for the displayed icon.

SUMMARY

In one embodiment, example systems and methods relate to a manner of controlling display attributes within a visual interface for enhancing stimuli and responses of a user. In various implementations, systems using stimuli on a visual interface that evoke a user response encounter difficulties highlighting a task while maintaining user awareness. For example, a system varying an icon color between black and white as stimuli causes user fatigue and decreases response accuracy on a visual interface. Therefore, in one embodiment, a control system varies display attributes of a visual interface at values and frequencies for generating stimuli that prevents user fatigue. In particular, the control system in a brain-machine interface (BMI) oscillates a display attribute (e.g., a color scheme or a background pattern) for an image layer at a frequency. The control system also oscillates display attributes at a harmonic of the frequency to enhance stimuli, while mitigating user fatigue. In one approach, the image layer is an icon and the oscillation toggles the display attribute between a pair of states (e.g., two colors). In one approach, the oscillation may continue until the control system receives a response (e.g., icon selection) through the BMI or an event (e.g., alert) ends. In this way, the control system produces stimuli in the visual interface while preventing user fatigue by oscillating display attributes using harmonic frequencies.

In one embodiment, a control system for changing display attributes within a visual interface for enhancing stimuli and responses of a user is disclosed. The control system includes a processor and a memory communicably coupled to the processor and storing a visualization module including instructions that, when executed by the processor, cause the processor to select display attributes related to a first layer of an image and a second layer of the image, wherein the image is associated with the interface to control a component. The instructions also include instructions to oscillate, at a frequency, between first values of the display attributes for displaying the first layer. The instructions also include instructions to oscillate, at a harmonic of the frequency, between second values of the display attributes for displaying the second layer in parallel with the first layer until detection of a selection associated with the interface.

In one embodiment, a non-transitory computer-readable medium for controlling display attributes within a visual interface for enhancing stimuli and responses of a user and including instructions that when executed by a processor cause the processor to perform one or more functions is disclosed. The instructions include instructions to select display attributes related to a first layer of an image and a second layer of the image, wherein the image is associated with the interface to control a component. The instructions also include instructions to oscillate, at a frequency, between first values of the display attributes for displaying the first layer. The instructions also include instructions to oscillate, at a harmonic of the frequency, between second values of the display attributes for displaying the second layer in parallel with the first layer until detection of a selection associated with the interface.

In one embodiment, a method for controlling display attributes within a visual interface for enhancing stimuli and responses of a user is disclosed. In one embodiment, the method includes selecting display attributes related to a first layer of an image and a second layer of the image, wherein the image is associated with an interface to control a component. The method also includes oscillating, at a frequency, between first values of the display attributes for displaying the first layer. The method also includes oscillating, at a harmonic of the frequency, between second values of the display attributes for displaying the second layer in parallel with the first layer until detecting a selection associated with the interface.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

DETAILED DESCRIPTION

Figure 1:
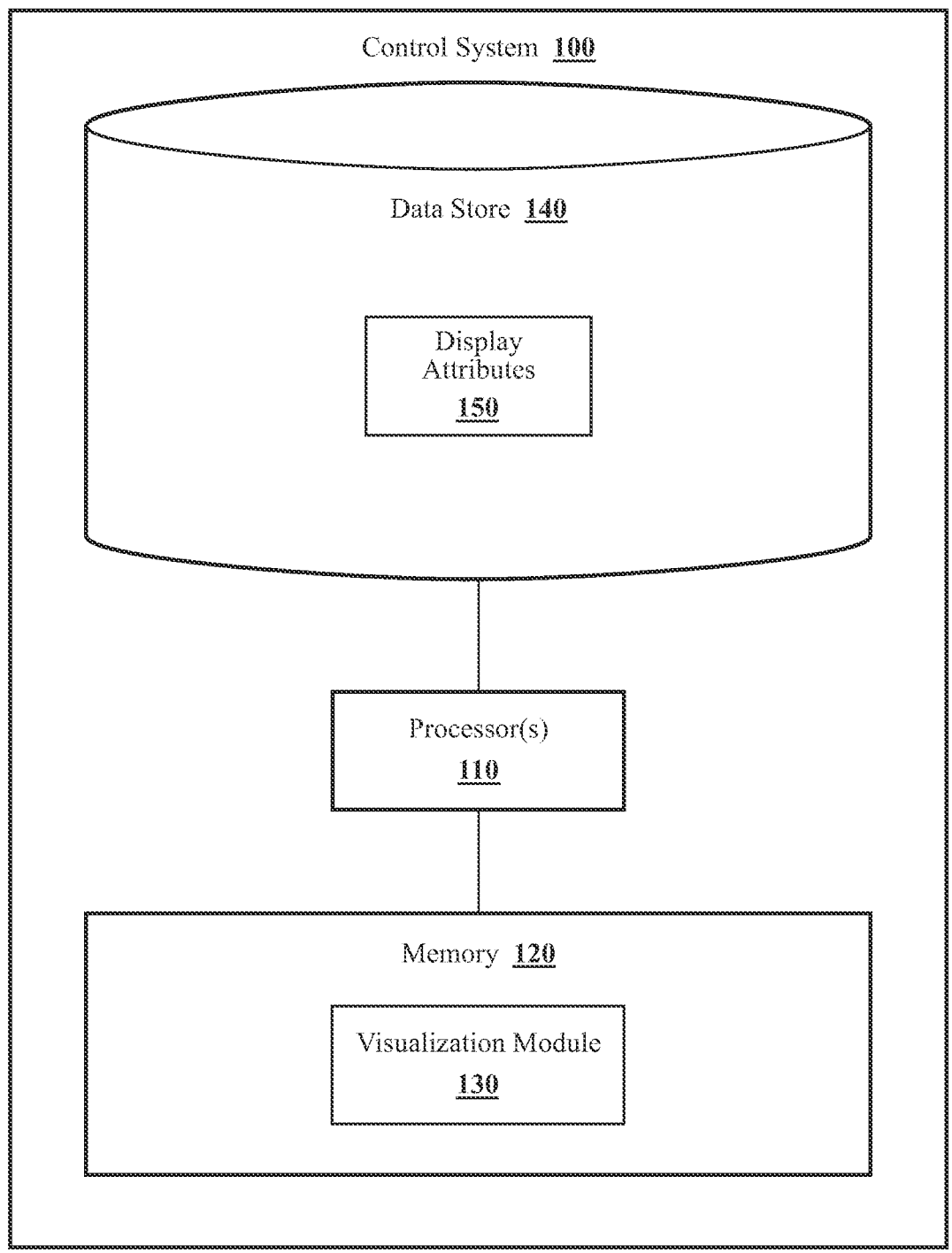
FIG. 1 illustrates one embodiment of a control system that is associated with varying display attributes of a visual interface as stimuli.

Systems, methods, and other embodiments associated with controlling display attributes within a visual interface for enhancing stimuli and responses of a user are disclosed herein. In various implementations, systems using stimuli on a visual interface for a visually evoked potential (VEP) scheme encounter difficulties executing a task while maintaining user responsiveness. For example, a system varying colors within an image between black and white as stimuli causes user fatigue and decreases accuracy on a brain-machine interface (BMI). Therefore, in one embodiment, a control system selects and varies display attributes on a visual interface for optimizing a VEP scheme using harmonic frequencies. Here, display attributes may define values about colors or backgrounds (e.g., patterns) for areas within an image. Furthermore, the control system can control different portions of the image by layer, where each layer is associated with an icon or background. As such, the control system can use a VEP scheme that enhances or increases responsiveness to parts (e.g., layers) of a visual interface while mitigating fatigue by oscillating colors beyond black and white.

Moreover, the control system oscillates the display attributes at a frequency (e.g., a fundamental frequency or a first harmonic). In one approach, the control system selects the frequency that enhances or increases a VEP response using cycles of the display attributes between ON/OFF frames (e.g., display frames). For example, an OFF frame represents disengaging an attribute to reduce stimuli and an ON frame may achieve the opposite effect. In one example, the control system displays the ON frame of icon backgrounds as orange while the OFF frame is green. As such, the control system may oscillate the colors through the ON/OFF frames at the frequency. In this way, the different colors maximize contrast between the ON/OFF frames for triggering robust VEP responses in the visual cortex of a user. Here, the control system measures the VEP response using electroencephalography (EEG) sensors of the BMI and also adjusts the frequency for optimizing the VEP response.

As further enhancements, in one example the control system uses higher harmonics of the frequency that optimizes the VEP scheme and mitigates user fatigue. In particular, the control system overlays the display attributes within layers of the image that oscillate at different frequencies, thereby creating a unique and a robust VEP scheme. In other words, the control system may oscillate two display attributes between different frames. For example, the control system uses a third color as an ON frame for oscillating a symbol color within an icon at the second harmonic of the frequency (e.g., a fundamental frequency). Here, the control system may oscillate in parallel an icon background between two colors at the frequency. In other words, the control system may oscillate two colors for the visual interface at the fundamental frequency between frames while oscillating a third color at the second harmonic. This sequence for a composed image can continue until the control system detects a selection on the visual interface or the BMI measures a target response from the user. In this way, the control system improves a VEP response and input accuracy for the visual interface while mitigating fatigue by using colors and harmonics.

With reference to FIG. 1, a control system 100 that varies display attributes of a visual interface as stimuli is illustrated. The control system 100 is shown as including a processor(s) 110 that executes instructions associated with controlling a visual interface In one embodiment, the control system 100 includes a memory 120 that stores a visualization module 130. The memory 120 is a random-access memory (RAM), read-only memory (ROM), a hard-disk drive, a flash memory, or other suitable memory for storing the visualization module 130. The visualization module 130 is, for example, computer-readable instructions that when executed by the processor(s) 110 cause the processor(s) 110 to perform the various functions disclosed herein.

Moreover, in one embodiment, the control system 100 includes a data store 140. In one embodiment, the data store 140 is a database. The database is, in one embodiment, an electronic data structure stored in the memory 120 or another data store and that is configured with routines that can be executed by the processor(s) 110 for analyzing stored data, providing stored data, organizing stored data, and so on. Thus, in one embodiment, the data store 140 stores data used by the visualization module 130 in executing various functions associated with varying (e.g., oscillate or toggle) or display attributes.

The data store 140 also includes the display attributes 150. In one approach, the display attributes 150 define values about colors, a color scheme, background colors, background patterns (e.g., checkered), frequency, and so on associated with an image. These values can be associated with an icon, a symbol, a background area, and so on within the image. Furthermore, the icon, the symbol, or the background may represent a layer of an image. In this way, the control system 100 can control different portions of the image by layer according to the display attributes 150.

As explained below, the visualization module 130, in one embodiment, is configured to perform tasks for varying the display attributes 150 within a visual interface as stimuli. For example, the visualization module 130 includes instructions that cause the processor(s) 110 to implement a visual scheme in a system (e.g., vehicle) using VEP. In systems using a VEP scheme, the control system 100 displays visual stimuli according to an oscillation frequency (e.g., a display refresh rate) for evoking a response. For instance, the visual cortex of a user responds to stimuli of display attributes according to the VEP scheme. Oscillating a display attribute in this manner is sometimes called a steady-state VEP (SSVEP) scheme. Furthermore, the control system 100 may use motion SSVEP (MSSVEP) when the oscillation includes animation or motion of a display attribute. In one approach, the user response is selecting or providing feedback by viewing a display attribute oscillating on a visual interface. For feedback or input, the control system 100 may measure responses to these visual stimuli using EEG sensors of a BMI. The EEG sensors are coupled to a body part (e.g., head) of a user and communicate measured stimuli to the control system 100 accordingly. In this way, the control system 100 measures effectiveness and accuracy to a VEP scheme.

In various implementations, the control system 100 is used for consumer electronics (CE), mobile devices, vehicles, and so on that benefit from the functionality discussed herein associated with controlling the display attributes 150 within a visual interface for enhancing stimuli and responses of a user. For instance, the control system 100 renders icons directly on a vehicle windshield, side-window, a heads-up display (HUD), and so on for driver control using a BMI according to the display attributes 150. The control system 100 uses measurements from EEG sensors on or near a body part of the operator to determine user feedback to stimuli. The control system 100 can vary display attributes (e.g., color contrast) of the icons at different frequencies for increasing focus, enhancing response time, or encouraging selection. For example, the visualization module 130 oscillates background display attributes of an icon between orange/green instead of black/white for producing effective while gentle stimuli. In this way, the control system 100 mitigates fatigue for the VEP scheme, particularly during extended exposure (e.g., extended road trips).

Figure 2:
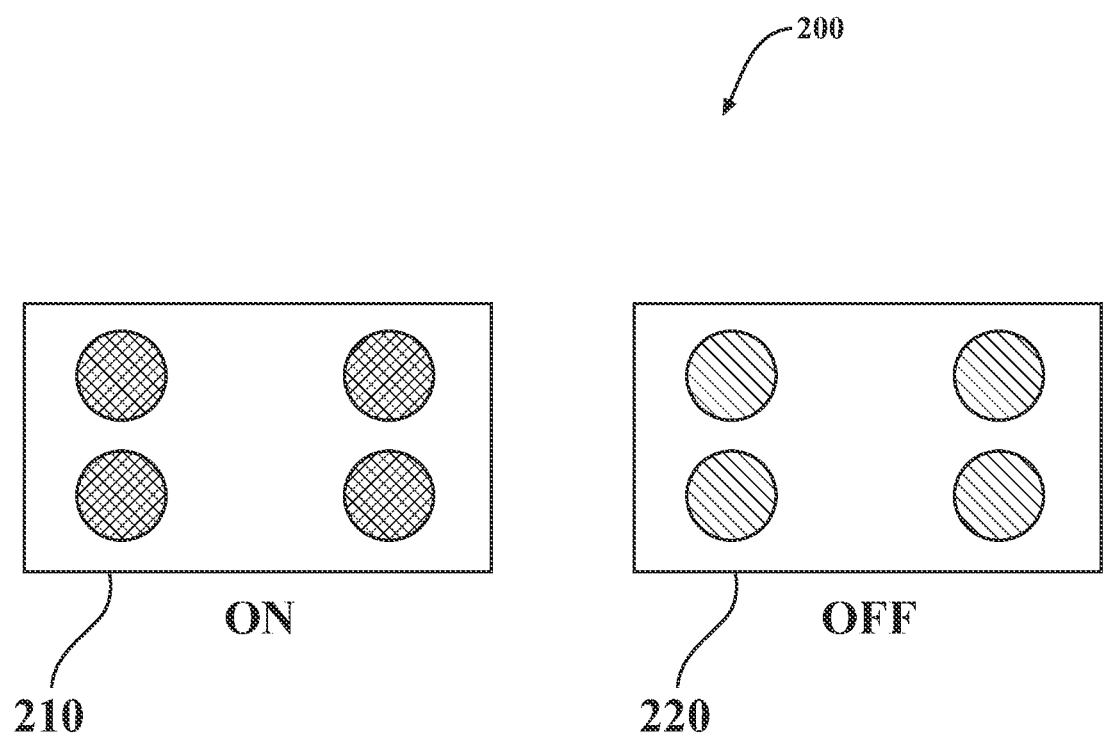
FIG. 2 illustrates one example of the control system of FIG. 1 varying colors within the visual interface as stimuli.

Turning now to FIG. 2 an example of the control system 100 varying colors within the visual interface 200 as stimuli are illustrated. Here, the visual interface 200 includes four icons. In one approach, the icons may be a music icon, a navigation icon, a settings icon, and a temperature icon that the visualization module 130 displays on a HUD of a vehicle. The control system 100 may vary the display attributes 150 of each icon separately by frequency (e.g., 8-15 Hertz (Hz)) within a BMI as a VEP scheme. The selected frequencies may depend on the refresh rate of a display (e.g., 60 Hz) and target cycles of display attributes between ON/OFF frames. The control system 100 may also select a frequency for oscillating a display attribute to attain a VEP response that is unique. For example, a duty cycle of 50% for a refresh rate at 60 Hz and an icon frequency at 10 Hz for 6 frames involves the control system 100 displaying 3 frames ON and 3 frames OFF. Similarly, an icon frequency at 15 Hz for 4 frames results in 2 frames ON and 2 frames OFF. In addition, the control system 100 can use measurements from EEG sensors of a BMI between these ON/OFF frames to adjust the frequency or duty cycle and calibrate the BMI. In one approach, the control system 100 can capture the oscillation of visual stimuli and adjust the frequency from the EEG data by calibrating the BMI or through incremental learning that continuously finds the optimal settings for the visual stimuli. In this way, the control system 100 can improve focus or responsiveness of a user for the VEP scheme through the adjustments.

For the visual interface 200, the control system 100 may use a VEP scheme that enhances stimuli while mitigating fatigue through different color pairs instead of black and white. The enhanced stimuli may improve input accuracy and focus of users for systems using a BMI. For example, the visualization module 130 displays the ON frame 210 of four icon backgrounds as orange while the OFF frame 220 is green within the visual interface 200. The control system 100 may then oscillate the colors of the icon backgrounds through these ON/OFF frames at a frequency that enhances a VEP and a corresponding user response. In other words, the different colors maximize contrast between the ON/OFF frames for triggering robust VEP responses in the visual cortex of a user. The user response may be the control system 100 drawing the focus and the attention of the user to an alert or event associated with the image for the BMI. The user response may also be the control system 100 evoking a selection associated with the image.

Figure 3:
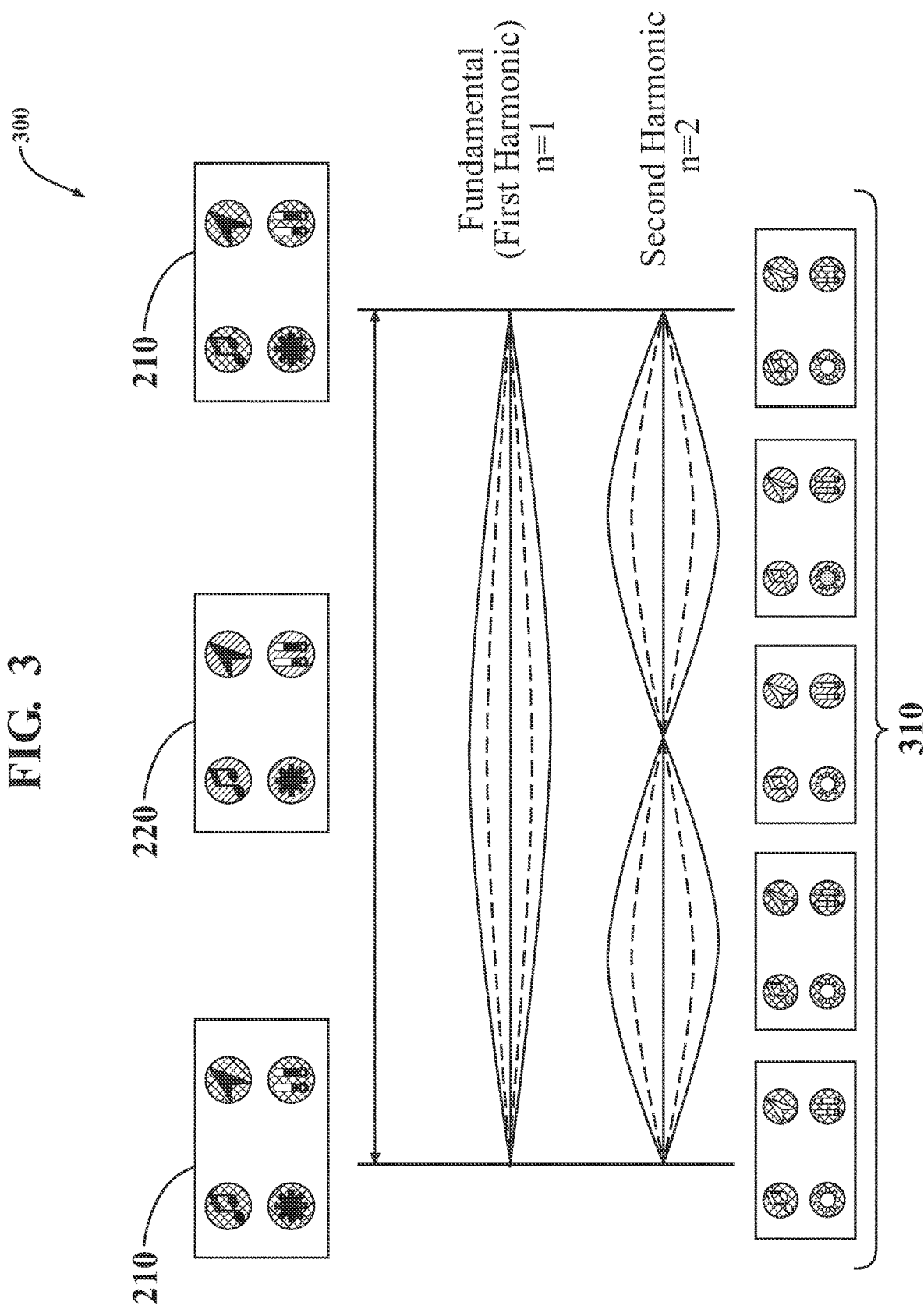
FIG. 3 illustrates one example of the control system varying colors and backgrounds within the visual interface as stimuli.

Referring to FIG. 3, one example of the control system 100 varying (e.g., oscillating or toggling) colors and backgrounds within the visual interface 300 as stimuli is illustrated. Here, the control system 100 may oscillate or toggle two display attributes between different frames. Although, in this example, the visual interface 300 has two display attributes that vary, the control system 100 may vary any number. In one approach, the control system 100 uses a third color as an ON frame for oscillating the symbol (e.g., lyric, arrow, gear, thermometer) color 310 within an icon at the second harmonic of the fundamental frequency. In parallel, the control system 100 oscillates the icon background at the fundamental frequency (i.e., first harmonic). In this example, the OFF frame of the symbol color 310 is white. As such, the control system 100 may oscillate two colors at the fundamental frequency between frames while oscillating the symbol color 310 at the second harmonic between frames. In other words, the two colors for the icon background may change between every other ON/OFF frames, whereas the symbol color changes every frame in the visual interface 300. In this way, the control system 100 improves a VEP response and input accuracy for the visual interface 300 while mitigating fatigue by using higher harmonics.

By overlaying the display attributes 150 within layers of an image and using higher harmonics, the control system 100 creates unique VEP schemes. Utilizing harmonic frequencies contributes to increased frequency band-power (e.g., micro volts^2/Hz) on the fundamental, second harmonic, or higher harmonics. The control system 100 also increases the information transfer rate (ITR) as well as VEP detection in shorter time windows (e.g., 2 seconds) by using higher harmonics.

In one approach, portions of the visual interface 300 vary according to the display attributes 150 for optimizing the VEP scheme and BMI. As such, a pattern of one icon background may oscillate between ON/OFF frames at a fundamental frequency while other icon backgrounds remain ON/OFF. As explained above, the control system 100 may then also oscillate the color of the icon symbol at the second harmonic of the fundamental frequency. Such a VEP scheme can improve accuracy for a user selecting an icon visually through the BMI.

In various implementations, the control system 100 oscillates the display attributes 150 of a navigation icon within the visual interface 300 on a HUD due to changing traffic patterns. Operation is improved by the user selecting the navigation icon instead of other icons and receiving further information about the traffic patterns. For added enhancements, the control system 100 may use this approach to calibrate the BMI and the HUD according to selection times and measured stimuli.

In addition to selecting inputs and other tasks, the control system 100 may oscillate the display attributes 150 in the visual interface 300 using harmonic frequencies for authentication. A brainwave pattern represents a unique signature for a user of a BMI. As such, the control system 100 determines a brainwave pattern using measurements from EEG sensors of a user viewing an image. The control system 100 implements a VEP scheme for accurate authentication by oscillating the display attributes 150 at higher harmonics of the fundamental frequency between frames to increase unique responses. For example, the control system 100 oscillates a symbol within the image using an atypical color at the second harmonic. Meanwhile, the background of the symbol oscillates using a checkered pattern and an atypical color at the third harmonic. In this way, authentication accuracy is increased using the VEP scheme by the control system 100 acquiring a robust brainwave pattern from the BMI through different harmonic frequencies.

Figure 4:
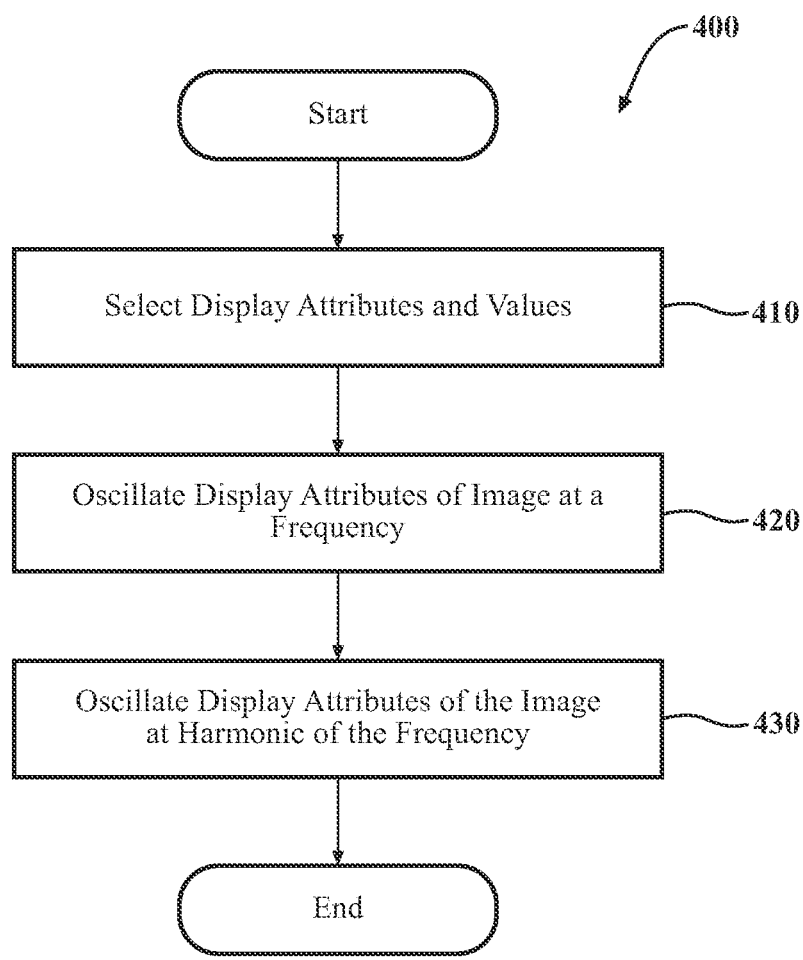
FIG. 4 illustrates one embodiment of a method that is associated with varying display attributes of the visual interface as stimuli.

Turning now to FIG. 4, a flowchart of a method 400 that is associated with controlling display attributes within a visual interface for enhancing stimuli and responses of a user is illustrated. Method 400 will be discussed from the perspective of the control system 100 of FIG. 1. While method 400 is discussed in combination with the control system 100, it should be appreciated that the method 400 is not limited to being implemented within the control system 100 but is instead one example of a system that may implement the method 400.

At 410, the control system 100 selects the display attributes and associated values to vary (e.g., oscillate or toggle) on a visual interface. In one approach, the display attributes define values about colors, a color scheme, background colors, or background patterns (e.g., checkered) associated with an image. These values can be for an icon, a symbol, a background area, and so on within the image. In various implementations, the icon, the symbol, or the background area may represent a layer of an image. In this way, the control system 100 can control different portions of the image by layer according to the display attributes.

Moreover, the control system 100 may select the display attributes to implement a VEP scheme specified by a manufacturer for a particular task. For example, a HUD displaying a temperature control system uses a VEP scheme that enhances or increases visual responses in a BMI to save energy by optimizing temperature adjustments. The control system 100 can also use a VEP scheme that increases focus on icon having an alert (e.g., badge) while mitigating fatigue by oscillating colors beyond black and white.

At 420, the control system 100 oscillates the display attributes and associated values selected on the visual interface at a frequency (e.g., a fundamental frequency or a first harmonic). In one approach, the control system 100 selects the frequency to attain a particular VEP response or meet the refresh rate of a display. As explained above, the frequency may also be related to target cycles of the display attributes between ON/OFF frames. In one approach, an OFF frame may represent disengaging an attribute to reduce stimuli and an ON frame may achieve the opposite effect. Furthermore, the control system 100 can use measurements from EEG sensors of a BMI to adjust the frequency or duty cycle and calibrate the BMI. In one approach, the control system 100 can capture the oscillation of visual stimuli and adjust the frequency from the EEG data by calibrating the BMI or through incremental learning that continuously finds the optimal settings for the visual stimuli. Accordingly, the control system 100 improves the responsiveness of a user through the adjustments for the VEP scheme.

In various implementations, the control system 100 uses a VEP scheme to enhance stimuli while mitigating fatigue through different color pairs. For example, the visualization module 130 displays the ON frame of icon backgrounds as orange while the OFF frame is green within a visual interface. The control system 100 may then oscillate the colors of the icon backgrounds through the ON/OFF frames at the frequency. In other words, the different colors maximize contrast between the ON/OFF frames for triggering robust VEP responses in the visual cortex of a user.

At 430, the control system 100 oscillates display attributes of the image at a harmonic (e.g., second harmonic) of the frequency. Here, using harmonics of the frequency optimizes responses to the VEP scheme while mitigating fatigue. In particular, the control system 100 overlays the display attributes within layers of an image that oscillate at different frequencies, thereby creating a unique and a robust VEP scheme. As such, the control system 100 may oscillate two display attributes between different frames. For example, the control system 100 uses a third color as an ON frame for oscillating a symbol color within an icon at the second harmonic of the frequency used to oscillate the icon background. Here, the OFF frame of the symbol color may be white. Accordingly, the control system 100 may oscillate two colors for the visual interface at the fundamental frequency between frames while oscillating the symbol color at the second harmonic. In this way, the control system 100 improves a VEP response and input accuracy for the visual interface while mitigating fatigue.

In various implementations, the pattern of one icon background may oscillate between ON/OFF frames at a fundamental frequency while other icon backgrounds remain in a current state. Meanwhile, the control system 100 oscillates the color of the icon symbol at the second harmonic of the fundamental frequency. This sequence for a composed image may continue until the control system 100 detects a selection on the visual interface or receives from the BMI a target response measured from the user. In other words, the control system 100 can use data from EEGs of the BMI to ensure that stimuli has increased beyond a threshold as a response and effect. Here, the effect may be viewing and physically processing a change on the visual interface. In another example, the control system 100 oscillates the display attributes 150 of a navigation icon within the visual interface on a HUD due to changing traffic patterns. This operation may continue until the user reacts by a driving maneuver, an input, or the control system 100 measures certain stimuli using the BMI. In this way, the control system 100 uses harmonic frequencies and a VEP scheme that improves accuracy and stimuli.

Detailed embodiments are disclosed herein. However, it is to be understood that the disclosed embodiments are intended as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Furthermore, the terms and phrases used herein are not intended to be limiting but rather to provide an understandable description of possible implementations. Various embodiments are shown in FIGS. 1-4, but the embodiments are not limited to the illustrated structure or application.

The flowcharts and block diagrams in the figures illustrate the architecture, functionality, and operation of possible implementations of systems, methods, and computer program products according to various embodiments. In this regard, a block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises the features enabling the implementation of the methods described herein and, which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Examples of such a computer-readable medium may include, but are not limited to, a floppy disk, a flexible disk, a hard disk, a magnetic tape, another magnetic medium, an application-specific integrated circuit (ASIC), a CD, another optical medium, a RAM, a ROM, a memory chip or card, a memory stick, and other media from which a computer, a processor or other electronic device can read. In the context of this document, a computer-readable storage medium may be any tangible medium that can contain, or store a program for use by or in connection with an instruction execution system, apparatus, or device.

The following includes definitions of selected terms employed herein. The definitions include various examples and/or forms of components that fall within the scope of a term and that may be used for various implementations. The examples are not intended to be limiting. Both singular and plural forms of terms may be within the definitions.

References to "one embodiment," "an embodiment," "one example," "an example," and so on, indicate that the embodiment(s) or example(s) so described may include a particular feature, structure, characteristic, property, element, or limitation, but that not every embodiment or example necessarily includes that particular feature, structure, characteristic, property, element, or limitation. Furthermore, repeated use of the phrase "in one embodiment" does not necessarily refer to the same embodiment, though it may.

"Module," as used herein, includes a computer or electrical hardware component(s), firmware, a non-transitory computer-readable medium that stores instructions, and/or combinations of these components configured to perform a function(s) or an action(s), and/or to cause a function or action from another logic, method, and/or system. Module may include a microprocessor controlled by an algorithm, a discrete logic (e.g., an ASIC), an analog circuit, a digital circuit, a programmed logic device, a memory device including instructions that, when executed perform an algorithm, and so on. A module, in one or more embodiments, includes one or more CMOS gates, combinations of gates, or other circuit components. Where multiple modules are described, one or more embodiments include incorporating the multiple modules into one physical module component. Similarly, where a single module is described, one or more embodiments distribute the single module between multiple physical components.

Additionally, module, as used herein, includes routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an ASIC, a hardware component of a system on a chip (SoC), as a programmable logic array (PLA), or as another suitable hardware component that is embedded with a defined configuration set (e.g., instructions) for performing the disclosed functions.

In one or more arrangements, one or more of the modules described herein can include artificial or computational intelligence elements, e.g., neural network, fuzzy logic, or other machine learning algorithms. Further, in one or more arrangements, one or more of the modules can be distributed among a plurality of the modules described herein. In one or more arrangements, two or more of the modules described herein can be combined into a single module.

Program code embodied on a computer-readable medium may be transmitted using any appropriate medium, including but not limited to wireless, wireline, optical fiber, cable, radio frequency (RF), etc., or any suitable combination of the foregoing. Computer program code for carrying out operations for aspects of the present arrangements may be written in any combination of one or more programming languages, including an object-oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all combinations of one or more of the associated listed items. As an example, the phrase "at least one of A, B, and C" includes A, B, C, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A control system for an interface, comprising:
   a processor; and
   a memory communicably coupled to the processor and storing:
   a visualization module including instructions that, when executed by the processor, cause the processor to:
   select display attributes related to a first layer of an image and a second layer of the image, wherein the first layer includes a symbol and the second layer represents a background of the symbol that are overlayed, and the image is associated with the interface to control a component;

oscillate, at a frequency, between first values of the display attributes representing colors that are different for displaying the first layer; and oscillate, at a harmonic of the frequency, between second values of a pattern for displaying the second layer in parallel with the first layer until detection of a selection associated with the interface.

2. The control system of claim 1, wherein the instructions to oscillate between the first values further include instructions to toggle different color schemes of the first layer between frames at the frequency.

3. The control system of claim 2, wherein the instructions to:

oscillate between the second values further include instructions to toggle the color schemes for each of the frames and different background patterns of the second layer that selectively skip between the frames according to the harmonic and changing band powers of the frames.

4. The control system of claim 1, wherein the first layer includes an icon with the symbol that is associated with a portion of the image and forms a display scheme.

5. The control system of claim 1, wherein the first values are a color scheme of the symbol that excludes black and white and the color scheme is associated with the first layer.

6. The control system of claim 1, wherein the frequency is different than a refresh rate of a device that displays the image.

7. The control system of claim 3, further including instructions to oscillate the image according to parameters that define a display pattern surrounding the symbol.

8. The control system of claim 1, wherein the first values and the second values define a pair of states to control the display attributes between frames of the image.

9. The control system of claim 1, wherein the component is an audio control device, a display, or a heads-up display (HUD).

10. A non-transitory computer-readable medium for controlling an interface comprising:

instructions that when executed by a processor cause the processor to:

select display attributes related to a first layer of an image and a second layer of the image, wherein the first layer includes a symbol and the second layer represents a background of the symbol that are overlayed, and the image is associated with the interface to control a component;

oscillate, at a frequency, between first values of the display attributes representing colors that are different for displaying the first layer; and oscillate, at a harmonic of the frequency, between second values of a pattern for displaying the second layer in parallel with the first layer until detection of a selection associated with the interface.

11. The non-transitory computer-readable medium of claim 10, wherein the instructions to oscillate between the first values further include instructions to:

toggle different color schemes of the first layer between frames at the frequency; and oscillate between the second values further include instructions to toggle the color schemes for each of the frames and different background patterns of the second layer that selectively skip between the frames according to the harmonic and changing band powers of the frames.

12. A method, comprising:

selecting display attributes related to a first layer of an image and a second layer of the image, wherein the first layer includes a symbol and the second layer represents a background of the symbol that are overlayed, and the image is associated with an interface to control a component;

oscillating, at a frequency, between first values of the display attributes representing colors that are different for displaying the first layer; and oscillating, at a harmonic of the frequency, between second values of a pattern for displaying the second layer in parallel with the first layer until detecting a selection associated with the interface.

13. The method of claim 12, wherein oscillating between the first values further includes toggling different color schemes of the first layer between frames at the frequency.

14. The method of claim 13, wherein oscillating between the second values further includes toggling the color schemes for each of the frames and different background patterns of the second layer that selectively skip between the frames according to the harmonic and changing band powers of the frames.

15. The method of claim 12, wherein the first layer includes an icon with the symbol that are associated with a portion of the image and forms a display scheme.

16. The method of claim 12, wherein the first values are a color scheme of the symbol that excludes black and white and the color scheme is associated with the first layer.

17. The method of claim 12, wherein the frequency is different than a refresh rate of a device that displays the image.

18. The method of claim 14, further comprising oscillating the image according to parameters that define a display pattern surrounding the symbol.

19. The method of claim 12, wherein the first values and the second values define a pair of states to control the display attributes between frames of the image.

20. The method of claim 12, wherein the component is an audio control device, a display, or a heads-up display (HUD).

* * * * *